US011801289B2

(12) United States Patent
Chu et al.

(10) Patent No.: US 11,801,289 B2
(45) Date of Patent: Oct. 31, 2023

(54) SUBUNIT VACCINE OF CONTAGIOUS CAPRINE PLEUROPNEUMONIA AND PREPARATION METHOD AND USE THEREOF

(71) Applicant: Lanzhou Veterinary Research Institute, Chinese Academy of Agricultural Sciences, Lanzhou (CN)

(72) Inventors: Yuefeng Chu, Lanzhou (CN); Shengli Chen, Lanzhou (CN); Huafang Hao, Lanzhou (CN); Xinmin Yan, Lanzhou (CN); Lina Ma, Lanzhou (CN); Yongsheng Liu, Lanzhou (CN)

(73) Assignee: Lanzhou Veterinary Research Institute, Chinese Academy of Agricultural Sciences, Lanzhou (CN)

( * ) Notice: Subject to any disclaimer, the term of this patent is extended or adjusted under 35 U.S.C. 154(b) by 2 days.

(21) Appl. No.: 17/335,573

(22) Filed: Jun. 1, 2021

(65) Prior Publication Data

US 2022/0233671 A1    Jul. 28, 2022

(30) Foreign Application Priority Data

Jan. 26, 2021    (CN) .......................... 202110110937.4

(51) Int. Cl.
*A61K 39/02* (2006.01)
*A61K 39/39* (2006.01)
*A61K 39/00* (2006.01)

(52) U.S. Cl.
CPC .......... *A61K 39/0241* (2013.01); *A61K 39/39* (2013.01); *A61K 2039/55566* (2013.01); *A61K 2039/55577* (2013.01); *A61K 2039/55588* (2013.01)

(58) Field of Classification Search
None
See application file for complete search history.

(56) References Cited

PUBLICATIONS

Dar et al. Vaccine. vol. 31, 2013,pp. 3327-3332. (Year: 2013).*
Yatoo et al. Vaccine vol. 7 No. 71 , pp. 1-21 , 2019, (Year: 2019).*
Zhao et al. Asian Journal of Animal and Veterinary Advances vol. 8, No. 22 , 2013 (Year: 2013).*
Ayelet et al. Small Research vol. 73, pp. 200-205, 2007 (Year: 2007).*
A0A1D5B4H3 MYCCC Li, W Submitted Dec. 2013 to the EMBL/GenBank? DDB# (Year: 2013), for SEQ IDs No. 1-5.*

* cited by examiner

*Primary Examiner* — Gary B Nickol
*Assistant Examiner* — Khatol S Shahnan Shah
(74) *Attorney, Agent, or Firm* — Jordan IP Law, LLC; Todd A. Vaughn

(57) ABSTRACT

The present disclosure provides a subunit vaccine of contagious caprine pleuropneumonia and preparation method and use thereof, belonging to the technical field of preparation of animal infectious disease vaccine. The combination of Mycoplasma capricolum subsp. capripneumoniae immunoproteins comprises Mycoplasma capricolum subsp. capripneumoniae immunoproteins A, B, C, D and E; the mass ratio of Mycoplasma capricolum subsp. capripneumoniae immunoproteins A, B, C, D and E is (0.5-1.5):(0.5-1.5):(0.5-1.5):(0.5-1.5):(0.5-1.5). The subunit vaccine of contagious caprine pleuropneumonia comprises the combination of Mycoplasma capricolum subsp. capripneumoniae immunoproteins and adjuvant; the subunit vaccine has the advantages of high safety, good immunization effect, high stability and minor adverse effects.

3 Claims, 2 Drawing Sheets
Specification includes a Sequence Listing.

SEQUENCE LISTING

```
<160> NUMBER OF SEQ ID NOS: 5

<210> SEQ ID NO 1
<211> LENGTH: 454
<212> TYPE: PRT
<213> ORGANISM: Artificial Sequence
<220> FEATURE:
<223> OTHER INFORMATION: Amino acid sequence of Mycoplasma capricolum
      subsp. capripneumoniae immunoprotein A

<400> SEQUENCE: 1

Met Lys Thr Lys Asn Gln Glu Glu Ile Pro Asn Gly Asp Ala Phe
1               5                   10                  15

Lys Gly Ala Lys Ser Leu Glu Lys Lys Leu Ser Pro Phe Ser Asp Asn
                20                  25                  30

Thr Ile Glu Thr Gln Gln Ala Gly Leu Ser Arg Val Phe Ile Lys Ala
            35                  40                  45

Ser Lys Lys Ala Tyr Ser Asn Asn Gln Asp Asp Phe Lys Asn Ala Ile
        50                  55                  60

Glu Arg Thr Gly Gly Leu Phe Ile Leu Asp Lys Asn Tyr Gln Asp Ile
```

```
            65                  70                  75                  80

Phe Phe Asn Glu Glu Leu Met Lys Ile Ile Gly Val Gly Val Tyr
                        85                  90                  95

Ser Lys Asn Ser Ser Asp Lys Arg Ile Asn Lys Lys Leu Thr Leu Glu
                    100                 105                 110

Glu Phe Leu Gly Glu Ala Lys Ala Glu Ser Leu Gln Pro Ala Asn Phe
                    115                 120                 125

Ser Asn Lys Asn Ser Pro Phe Val Ser Phe Asn Leu Lys Asn Glu Tyr
                130                 135                 140

Leu Lys Asn Leu Ile Asp Pro Lys Lys Asn Lys Asp Asn Asn Ser Leu
        145                 150                 155                 160

Thr Met Ile Thr Ser Val Gly His Val Ile Glu Thr Leu Arg Thr Tyr
                        165                 170                 175

Tyr Lys Lys Ala Asn Ser Thr Asn Lys Gln Val Ile Glu Lys Tyr Leu
                    180                 185                 190

Asn Thr Tyr Phe Asn Gln Ile Ile Lys Pro Ile Gln Asp Tyr Ile Ser
                    195                 200                 205

Ser His Leu Ser Asp Ala Leu Ala Val Lys Thr Leu Lys Asp Leu Phe
                210                 215                 220

Ser Ile Glu Tyr Ser Thr Thr Thr Glu Gly Thr Ser Gly Asn Leu
        225                 230                 235                 240

Ala Ile Gln Arg Thr Ser Leu Val Asp Ser Lys Ile Asn Lys Trp Trp
                        245                 250                 255

Lys Ser Asn Gln Thr Gly Lys Ile Glu Asn Thr Ser Asp Leu Lys Tyr
                    260                 265                 270

Val Leu Phe Gly Thr Asn Asn Leu Asp Lys Lys Asn Asp Arg His Ile
                    275                 280                 285

Phe Arg Phe Thr Asn Ser Ala Asn Lys Phe Leu Tyr Asp Ala Asn Ala
                290                 295                 300

Ser Glu Lys Asp Phe Ile Lys Asp Asp Lys Gly Asn Val Gly Lys Tyr
        305                 310                 315                 320

Tyr Asn Lys Leu Lys Ile Ser Ser Asp Asn Ser Ile Ser Gln Asp Glu
                        325                 330                 335

Glu Leu Asp Tyr Ile Asp Lys Val Ser Asn Lys Leu Ile Ser Ile Ile
                    340                 345                 350

Met Thr Glu Ile Leu Phe Lys Lys Asp Thr Thr Asp Lys Asp His Val
                    355                 360                 365

Val Asn Arg Asn Leu Asp Gln Ala Leu Phe Arg Asn Asn Val Leu Leu
                370                 375                 380

His Asn Asn Gln Ile Ser Pro Asp Asn Thr Arg Ile Val Thr Thr Asn
        385                 390                 395                 400

Pro Ala Ile Val Thr Asp Arg Lys Thr Gln Thr Thr Lys Leu Tyr Ile
                        405                 410                 415

Pro Val Trp Ser Asn Thr Met Ala Lys Gln Val Glu Ser Asp Ile Leu
                    420                 425                 430

Gln Thr Ser Leu Gly Tyr Thr Phe Lys Val Leu Ser Ile Lys Glu Phe
                    435                 440                 445

Ser Ser Asp Ile Leu Glu
                450

<210> SEQ ID NO 2
<211> LENGTH: 338
<212> TYPE: PRT
<213> ORGANISM: Artificial Sequence
```

```
<220> FEATURE:
<223> OTHER INFORMATION: Amino acid sequence of Mycoplasma capricolum
      subsp. capripneumoniae immunoprotein B

<400> SEQUENCE: 2

Met Ser Asn Ser Ser Asp Gln Ile Thr Asn Phe Tyr Lys Gln Lys
1               5                   10                  15

Gln Asp Gln Ile Ala Glu Val Lys Leu Ser Asn Lys Gln Asp Leu Glu
                20                  25                  30

Tyr Tyr Ser Leu Arg Asp Glu Tyr Ile Leu Phe Asn Gln Tyr Gln Val
            35                  40                  45

Asn Thr Gly Leu Cys Trp Asp Phe Ala Ser Ile Lys Ser Leu Glu Thr
50                  55                  60

Ala Leu Met Leu Ala Asn Asn Glu Met Tyr Asp Phe Ser Glu Ala Ser
65                  70                  75                  80

Ile Ser Val Leu Asn Glu His Trp Val Ala Asp Gly Val Phe Phe Arg
                85                  90                  95

Thr Phe Asp Asn Leu Leu Asn Arg Asn Gly Ile Ala Phe Glu Ser Asp
                100                 105                 110

Phe Arg Phe Gly Asp Leu Tyr Tyr Phe Pro Asn Thr Gly Ile Tyr Tyr
            115                 120                 125

Asp Lys Leu Leu Asp Leu Tyr Lys Ser Lys Tyr Ile Thr Asn Leu Ala
130                 135                 140

Asn Lys Leu Glu Ala Tyr Ser Phe Tyr Arg Tyr Ser Ile Leu Glu Lys
145                 150                 155                 160

Leu Lys Gln Ile Lys Glu His Ile Ser Lys His Ser Ala Leu Phe Val
                165                 170                 175

Gly Ile Asp His Trp Gln Val Val Lys Asn Lys Val Asn Lys Gln Glu
                180                 185                 190

Thr Phe Gln Ile Thr Ser Gly Ser Met Gly Ala His Ala Val Ser Ile
            195                 200                 205

Ile Gly Trp Asp Asp Asn Tyr Ile Asn Asn Asp Ser Lys Gly Ala
                210                 215                 220

Phe Ile Val Leu Asn Ser Asp Gly Phe Tyr Asp Asn Asn Asp Gly Val
225                 230                 235                 240

Asn Tyr Leu Pro Tyr Asn Ser Ser Thr Ile Tyr Leu Asp Leu Gln Gly
                245                 250                 255

Tyr Lys Phe Ile Gly Asp Lys Leu Ile Ser Ser Lys Gly Ile Asn Ser
                260                 265                 270

Ser Ile Lys Asn Lys Tyr Phe Asn Tyr Asn Thr Lys Leu Ala Lys
            275                 280                 285

Lys Tyr Thr Glu Thr Lys Pro Leu Asn Gln Asn Val Phe Ser Trp Asp
    290                 295                 300

Asp Gln Val Glu Ile Gln Tyr Gln Leu Asn Asp Gln Ile Ala Asp Phe
305                 310                 315                 320

Lys Arg Ile Gln Thr Ser Ile Phe Leu Trp Gln Thr Arg Cys Phe Arg
                325                 330                 335

Leu Glu

<210> SEQ ID NO 3
<211> LENGTH: 909
<212> TYPE: PRT
<213> ORGANISM: Artificial Sequence
<220> FEATURE:
<223> OTHER INFORMATION: Amino acid sequences of Mycoplasma capricolum
      subsp. capripneumoniae immunoprotein C
```

<400> SEQUENCE: 3

```
Met Ser Thr Thr Ser Ile Glu Lys Leu Gly Arg Lys Asn Phe Val Asp
1               5                   10                  15

Glu Glu Ser Phe Lys Asn Ala Phe Ile Asp Pro Asn Ala Leu Pro Val
            20                  25                  30

Thr Glu Phe Ser Glu Val His Asn Asn Lys Arg Ser Val Lys Tyr Asp
                35                  40                  45

Pro Glu Lys Asn Val Val Lys Phe Asn Gly Lys Glu Ile Ser Val Asp
            50                  55                  60

Gln Tyr Leu Gln Gln Tyr Tyr Gln Lys Tyr Gln Ala Leu Pro Tyr Leu
65                  70                  75                  80

Asn Ile Arg Tyr Gly Ser Phe Asn Phe Tyr Asn Gln Tyr Ile Glu Ala
                85                  90                  95

Val Ser Pro Gln Glu Phe Tyr Lys Phe Thr Lys Trp Phe Met Lys Asn
            100                 105                 110

Val Ser Trp Gly Pro Glu Ile Ile Thr Leu Lys Ser Phe Ser Ile Val
            115                 120                 125

Lys Gly Val Glu Met Ser Gly Asn Ser Ile Thr Leu Gly Ala His Ser
130                 135                 140

Asn Lys Asn Lys Glu Glu Thr Thr Ile Lys Phe Tyr Pro Asp Ala Phe
145                 150                 155                 160

Phe Gly Thr Leu Pro Ile Tyr Ser Asn Leu Ser Gly Arg Gly Asn Ala
                165                 170                 175

Tyr Glu Ser Leu Thr Tyr Lys Leu Asn Gln Gln Val Leu Thr Gln Lys
            180                 185                 190

Asp Leu Glu Gly Phe Leu Ala Asn Val Gly Asn Tyr Asn Ser Leu Val
            195                 200                 205

Asn Leu Ser Gln Gln Thr Ile Asn Lys Ser Tyr Phe Arg Gly Ile Thr
            210                 215                 220

Asn Val Ser Phe Leu Lys Gly Gln Lys Val Phe Ala Tyr Lys Gln Glu
225                 230                 235                 240

Asn Trp Gln Ser Lys Phe Ser Lys Thr Tyr Ser Glu Leu Glu Lys Lys
                245                 250                 255

Arg Leu Glu Asp Arg Ser Ser Tyr Leu Phe Val Ile Pro Ala Asn Ser
            260                 265                 270

Leu Gln Glu Ala Arg Lys Lys Leu Glu Val Lys Leu Ser Glu Tyr Lys
            275                 280                 285

Lys Glu Ser Asp Pro Phe Asn Phe Phe Glu Lys Ile Asn Pro Lys Asn
290                 295                 300

Val Val Leu Glu Glu Lys Thr Ile Ser Asp Ala Glu Val Lys Gln Asp
305                 310                 315                 320

Asn Thr Asn Lys Ile Ile Asp Lys Lys Leu Val Leu Thr Phe Asn Asp
                325                 330                 335

Lys Thr Asn Tyr Ile Ile His Asn Ala Phe Ser Asp Val Leu Thr Glu
            340                 345                 350

Gln Met Thr Ser Asn Asn Arg Arg Thr Tyr Val Ala Leu Lys Asn Tyr
            355                 360                 365

Val Asn Phe Ser Ser Ala Lys Gln Lys Leu Glu Asp Lys Val Lys Asn
            370                 375                 380

Phe Ile Leu Gln Ile Lys Glu Asn Ile Lys Leu Lys Ser Asn Gly Lys
385                 390                 395                 400

Glu Lys Glu Leu Glu Glu Leu Leu Lys Glu Phe Glu Ser Tyr Asn Asn
```

```
                405                 410                 415
Val Val Ser Leu Leu Glu Gln Lys Asn Leu Thr Ser Asp Ile Leu Lys
            420                 425                 430

Lys Val Asp Lys Lys Ile Phe Glu Ser Glu Thr Lys Phe Asn Gln Ile
            435                 440                 445

Leu Asn Lys Pro Asn Ser Asn Lys Thr Phe Asn Glu Lys Glu Tyr Tyr
            450                 455                 460

Lys Thr Asp Ile Ala Tyr Ser Leu Pro Glu Leu Ile Thr Leu Glu Thr
465                 470                 475                 480

Leu Val Gln His Asn Asn Ser Asn Lys Leu Asn Trp Arg Asp Phe Tyr
            485                 490                 495

Asn Leu Asn Glu Phe Val Ala Asp Arg Ser Asn Ile Leu Lys Asn Gly
            500                 505                 510

Ser Thr Glu Phe Phe Val Tyr Ser Lys Phe Val Lys Glu Ile Asn Ala
            515                 520                 525

Asn Glu Asn Lys Lys Tyr Glu Glu Leu Lys Ser Glu Asn Asp Leu Ile
            530                 535                 540

Ala Ala Ser Ser Lys Val Glu Leu Ile Asp Ile Leu Thr Lys Lys Ser
545                 550                 555                 560

Ile Ile Lys Pro Asn Ile Ser Gln Glu Glu Ile Asn Lys Ile Ile Leu
            565                 570                 575

Lys Val Asp Leu Phe Asp Leu Lys Lys Glu Gly Gln Asn Leu Leu Ile
            580                 585                 590

Ser Leu Arg Asn Thr Thr Ala Glu Lys Ala Ser Asn Lys Glu Lys Phe
            595                 600                 605

Gly Asn Lys Trp Ile Asn Ile Ser Ile Asn Ala Asn Ala Lys Lys Asp
            610                 615                 620

Val Ile Arg Ala Thr Asn Asp Leu Phe Ala Val Leu Glu Tyr Lys Lys
625                 630                 635                 640

Val Val Val Pro Ser Val Leu Lys Glu Glu Ser Asp Leu Arg Asn Pro
            645                 650                 655

Ile Thr Asn Lys Leu Glu Lys Thr Phe Asp Val Phe Val Asp Ala Tyr
            660                 665                 670

Glu Asn Leu Ile Asp Glu Leu Leu Glu Lys Val Leu Tyr Ala Ala Gln
            675                 680                 685

Trp Leu Glu Gly Pro His Ile Lys Lys Val Leu Asp Glu Asn Gly Val
            690                 695                 700

Met Gln Tyr Lys Leu Glu Asn Gly Lys Tyr Leu Gly Phe Thr Lys Asp
705                 710                 715                 720

Asp Arg Ile Gly Leu Trp Ala Ile Leu Lys Met Ser Asp Asn Asn Phe
            725                 730                 735

Lys Gly Ile Ser Thr Asp Phe Leu Lys Phe Val Gly Ala His Glu Tyr
            740                 745                 750

Gly His His Ile Thr Leu Asn Gly Ala Gln Asp Leu Gly Asn Lys Gly
            755                 760                 765

Ser Asp Pro Ile Phe Ile Ser Ala Leu Thr Pro Gly Ala Thr Pro Asp
            770                 775                 780

Ile Ser Asn Tyr Tyr Asn Arg Glu Val Val Asp Leu Phe Leu Lys Ala
785                 790                 795                 800

Arg Thr His Ile Lys Leu Glu Thr Lys Arg Leu Leu Asp Gln Phe Gly
            805                 810                 815

Ala Ile Lys Asp Tyr Gly Glu Tyr Ala Val Phe Asn Phe Ala Lys Lys
            820                 825                 830
```

Asp Lys Asn Gly Asn Ile Asn Phe Asp Thr Lys Asp Asn Ile Gly Ile
        835                 840                 845

Glu Lys Asp Ser Asp Ile Trp Gly Val Asp Ile Glu Asp Pro Asn Ile
850                 855                 860

Arg Lys Ala Leu Ser Asn Lys Lys Arg Phe Leu Gln Asp Phe Ala
865                 870                 875                 880

Gly Leu Leu Ala Ala Val Lys Glu Arg Gln Lys Glu Asn Asn Leu Thr
                885                 890                 895

Thr Asp Asp Asp Lys Lys Trp Leu Ser Ala Phe Leu Glu
                900                 905

<210> SEQ ID NO 4
<211> LENGTH: 1014
<212> TYPE: PRT
<213> ORGANISM: Artificial Sequence
<220> FEATURE:
<223> OTHER INFORMATION: Amino acid sequence of Mycoplasma capricolum
      subsp. capripneumoniae immunoprotein D

<400> SEQUENCE: 4

Met Thr Leu Asn Pro Thr Val Asn Ser Ser Asp Gln Gln Asn Gln Val
1               5                   10                  15

Val Lys Tyr Met Tyr Lys Asp Lys Lys Gly Val Leu Arg Phe Gln Pro
            20                  25                  30

Ala Ser Leu Lys Met Leu Asp Gly Ile Leu Lys Asp Gly Lys Gly Asn
        35                  40                  45

Pro Ile Lys Phe Asp Ile Ser Asn Asn Gly Lys Ser Val Glu Pro Ile
50                  55                  60

Val Val Lys Gly Gln Lys Asp Ser Glu Gly Lys Tyr Tyr Lys Ile Asp
65                  70                  75                  80

Glu Val Leu Val His Asn Lys Asp Gly Ser Pro Ile Ile Asn Val Pro
                85                  90                  95

Ile Gly Val Asn Leu Arg Asp Glu Asn Ser Gly Tyr Asn Asp Lys Lys
            100                 105                 110

Thr Ile Asp Phe Ile Asn Glu Lys Ile Lys Val Val Glu Ser Thr Ile
        115                 120                 125

Lys Ser Leu Val Val Asp Lys Tyr Ser Ile Asn Gly Trp Asn Asn Glu
130                 135                 140

Asn Thr Arg Ile Ser Leu Asp Ser Lys Ile Asp Leu Asn Tyr Pro Ala
145                 150                 155                 160

Ile Lys Asn Ile Phe Gly Ser Lys Val Pro Asn Asn Val Ser Glu Met
                165                 170                 175

Tyr Lys Asn Ile Tyr Ala Asp Tyr Val Leu Asn Arg Asp Val Asp Lys
            180                 185                 190

Gly Ser Tyr Lys Phe Asp Glu His Gly Glu Ile Ser Lys Val Lys Tyr
        195                 200                 205

Tyr Asn Leu Asp Ser Thr Lys Val Asp Arg Tyr Asn Ser Asp Thr
210                 215                 220

Pro Ser Ser Leu Ile Tyr Ala Asn Pro Ser Asn Tyr Lys Ile Thr Asp
225                 230                 235                 240

Asp Asn Val Glu Leu Asp Phe Lys Thr Ile Leu Trp Thr Leu Tyr Ala
                245                 250                 255

Ala Gly Phe Val Thr Tyr Gly Asn Leu Ile Asn Ala Gly Ser Ser Gln
            260                 265                 270

Val Leu Trp Leu Ser Lys Asp Lys Met Tyr Met Pro Asn Val Lys Leu 275                 280                 285
Gln Glu Ala Tyr Thr Asp Leu Tyr Phe Leu Ser Ser Leu Pro Lys Glu
            290                 295                 300

Tyr Glu Gln Ile Phe Glu Ala Lys Lys Val Leu Lys Trp Ile Ser Lys
305                 310                 315                 320

Tyr Thr Pro Leu Phe Ile Ser Ser Ser Asn Lys Thr Gly Val Trp
                325                 330                 335

Asn Met Ile Asp Asn Glu Gly Lys Phe Val Asp Phe Asn Leu Leu Ile
            340                 345                 350

Asn Glu Asn Phe Thr Asn Ser Ile Lys Leu Gln Leu Asn Tyr Ser Arg
            355                 360                 365

Val Lys Thr Leu Asp Ser Asn Val Leu Asn Gly Leu Phe Gly Thr Phe
            370                 375                 380

Lys Asp Phe Asn Asp Asn Ser Leu Glu Phe Asp Glu Tyr Asp Lys Trp
385                 390                 395                 400

Leu Asp Phe Val Thr Val Asp Leu Arg Lys Ala Lys Tyr Asn Gln Lys
                405                 410                 415

Gln Asp Arg Val Asp Trp Glu Ile Asp Tyr Val Lys Ser Lys Val Asp
            420                 425                 430

Ile Asp Lys Phe Lys Glu Lys Tyr Lys Ser Glu Val Leu Asp Lys Leu
            435                 440                 445

Asp Ser Ile Ser Ser Met Asn Asp Asn Gln Lys Gln Ala Phe Lys Thr
450                 455                 460

Phe Tyr Glu Lys Ala Asn Ala Asp Lys Thr Glu Gln Ile Trp Ala Asn
465                 470                 475                 480

Glu Ile Met Arg Arg Phe Ser Ser Tyr Phe Ala Met Tyr Asn Ser
                485                 490                 495

Ala Leu Ser Ile Gly Glu Ile Glu Ser Asn Lys Asp Leu Ala Trp Ile
            500                 505                 510

Phe Asp Ser Thr His Gly Tyr Gly Asp Phe Lys Lys Ala Lys Phe Lys
            515                 520                 525

Ile Lys Asn Pro Asp Lys Ser Lys Trp Glu Ile Ser Thr Asp Asp Leu
            530                 535                 540

Leu Asn Ala Tyr Lys Lys Leu Ala Lys Asp Leu Gly Val Glu Thr Lys
545                 550                 555                 560

Gln Leu Asn Leu Val Asp Ser Leu Val Phe Asp Asn Lys Thr Gln Leu
                565                 570                 575

Tyr Thr Asp Gln Thr Met Thr His Ile Tyr Asn Arg Lys Phe Asp Leu
            580                 585                 590

Leu Ser Ile Phe Ser Ser Leu Ala Thr Ala Gln Phe His Thr Ser Pro
            595                 600                 605

Thr Arg Asp Val Leu Asp Tyr Phe Tyr Lys Lys Thr Glu Arg Lys Val
            610                 615                 620

Asn Glu Leu Phe Ser Asn Tyr Thr Tyr Asn Phe Ala Glu Val Ile Asn
625                 630                 635                 640

Arg Asp Asn Leu Gln Ile Thr Tyr Ser Pro Ser Asn His Asp Phe Gly
                645                 650                 655

Asn Met Pro Ser Phe Leu Ser Asn Ile Ser Glu Ala Thr Thr Gly Leu
            660                 665                 670

Glu Tyr Val Val Asp Gly Thr Thr Thr Ala Lys Trp Lys Lys Arg Ala
            675                 680                 685

Ile Lys Ile Asn Asp Arg Asn Gly Arg Asn Gly Ile Val Asn Ala Ile
            690                 695                 700

```
Leu Asp Tyr Glu Lys Leu Val Asp Ser Glu Ala Lys Asn Lys Ala Glu
705                 710                 715                 720

Ala Leu Asn Leu Lys Tyr Arg Asn Ser Lys Leu Ser Gln Lys Ser Asn
                725                 730                 735

Leu Ser Asp Asp Ser Asn Tyr Asp Asn Ser Tyr Phe Gly Lys Phe Gln
            740                 745                 750

Ser Ile Asn Asn Gly Trp Phe Lys Asp Arg Trp Tyr Arg Asp Phe Leu
        755                 760                 765

Asp Phe Lys Leu Tyr Asp Asp Asn Gly Asn Pro Ile Lys Asp Glu Thr
    770                 775                 780

Ile Arg Ile Lys Asp Leu Glu Gly Lys Lys Val Asp Ser Arg Val Asn
785                 790                 795                 800

Ala Phe Trp Gln Phe Tyr Ile Gln Ser Gln Gly Val Gly Lys Arg Asn
                805                 810                 815

Ile Ser Gly Ile Trp Arg Asp Ala Asn Lys Asp Ala Val Ala Met Phe
            820                 825                 830

Gly Tyr Leu Ser Ser Asp Val Ala Asn Lys Ala Asn Tyr Leu Ala Phe
        835                 840                 845

Lys Asn Gln Lys Thr Gly Glu Ile Lys Thr Ile Lys Ile Asn Lys Gln
    850                 855                 860

Phe Ser Ser Asn Met Phe Tyr Tyr Lys Thr Gln Asn Ile Glu Asn Glu
865                 870                 875                 880

Ala Lys Tyr Glu Ala Ala Lys Thr Gln Glu Glu Lys Asp Lys Ile Arg
                885                 890                 895

His Thr Leu Ala His Glu Lys Tyr Asn Tyr Lys Asp Ile Asn Gly Gln
            900                 905                 910

His Thr Gly Val Gly Phe Val Ser Trp Val Ser Asp Tyr Ala Ile Met
        915                 920                 925

Ser Lys Tyr Lys Asn Ala Leu Leu Thr Pro Gly Gln Gln Tyr Ser Val
    930                 935                 940

Tyr Phe Ser Ser Asp Gln Lys Gly Thr Lys Asp Ile Ile Lys Thr Asp
945                 950                 955                 960

Leu Gly Asn Phe Glu Ser Ile Ala Glu Asn Gly Lys Thr Phe Ser Gln
                965                 970                 975

Ala Pro Val Arg Met Gln Lys Asn Lys Gln Val Ala Lys Val Asp Lys
            980                 985                 990

Asp Gly Thr Lys Tyr Tyr Glu Asn Thr Leu Tyr Val Tyr Asp Gln Phe
        995                 1000                1005

Asn Gly Val Lys Leu Glu
        1010

<210> SEQ ID NO 5
<211> LENGTH: 674
<212> TYPE: PRT
<213> ORGANISM: Artificial Sequence
<220> FEATURE:
<223> OTHER INFORMATION: Amino acid sequence of Mycoplasma capricolum
      subsp. capripneumoniae immunoprotein E

<400> SEQUENCE: 5

Met Lys Ser Gln Gly Asn Phe Ile Ser Tyr Lys Gln Glu Asn Ser Ser
1               5                   10                  15

Ser Ser Ser Gly Thr Ser Ser Gly Gly Ser Asp Thr Gly Ala Gly Arg
            20                  25                  30

Asn Thr Asp Thr Gly Ser Gly Ser Asn Gly Gly Phe Glu Thr Phe Asn
```

```
                35                  40                  45
Thr Arg Arg Asn Arg Glu Lys Asp Pro Ser Phe Asn Thr Phe Lys Glu
 50                  55                  60
Thr Ile Lys Glu Lys Leu Lys Lys Gly Ile Glu Val Lys Lys Glu
 65                  70                  75                  80
Ile Asp Ser Phe Leu Asp Lys Glu Ile Lys Ile Gly Asp Leu Lys
                 85                  90                  95
Thr Pro Asp Asp Lys Asn Lys Tyr Phe Glu Lys Ile Glu Arg Lys Thr
                100                 105                 110
Tyr Leu Thr Glu Leu Lys Lys Phe Phe Asp Lys Lys Asp Ser Asn Ser
                115                 120                 125
Phe Val Asp Lys Pro Asp Glu Phe Gly Phe Asn Ile Ser Phe Pro Tyr
                130                 135                 140
Ile Ile Ala Asn Leu Glu Lys Leu Tyr Thr Ala Thr Val Lys Phe Asp
145                 150                 155                 160
Gly Lys Asp Tyr Ser Asp Ile Lys Val Gly Lys Ser Gly Asp Ser Ala
                165                 170                 175
Lys Asp Ile Lys Gly Ser Asp Lys Lys Leu Asp Tyr Ser Asp Val Ile
                180                 185                 190
Thr Asn Asp Val Gly Lys Ile Ile Thr Asp Thr Lys Ala Gln Asp Asn
                195                 200                 205
Phe Ile Asn Ser Lys Glu Phe Asp Asp Val Val Lys Gly Tyr Leu Ala
                210                 215                 220
Thr Trp Lys Asn Glu Val Lys Lys Met Ile Tyr Gln Lys Gln Asp Ile
225                 230                 235                 240
Leu Glu Phe Gly Lys Asp Ile Phe Phe Glu Pro Thr Asn Gly Asn Thr
                245                 250                 255
Thr Thr Ser Glu Asn Thr Thr Gln Val Asp Gln Tyr Lys Val Tyr Leu
                260                 265                 270
Asp Thr Lys Lys Tyr Lys Ser Trp Ser Glu Tyr Ile Lys Glu Lys Ile
                275                 280                 285
Ser Lys Arg Phe Thr His Phe Asp Leu Glu Gln Asn Gln Lys Phe Lys
                290                 295                 300
Ile Val Asp Glu Ala Lys Pro Thr Pro Thr Pro Thr Lys Pro Thr Leu
305                 310                 315                 320
Pro Asp Pro Thr Asn Lys Pro Leu Val Pro Thr Asn Pro Pro Ser Ser
                325                 330                 335
Gln Ile Thr Gln Ala Val Glu Ala Leu Pro Asn Leu Glu Pro Tyr Ile
                340                 345                 350
Asn Tyr Gln Phe Ala Ser Tyr Asp Leu Ser Ser Ile Gly Ser Gln Leu
                355                 360                 365
Ser Ser Ser Gln Asp Glu Glu Lys Asp Lys Tyr Phe Phe Leu Asn
                370                 375                 380
Pro Ile Asn Thr Arg Phe Lys Tyr Thr Val Asp Ser Val Asn Gly Asn
385                 390                 395                 400
Ser Val Val Arg Ile Thr Asp Gln Ala Lys Ser Gly Asn Ser Arg
                405                 410                 415
Thr Tyr Ile Tyr Glu Asn Val Gln Val Gly Lys Asp Trp Arg Phe Leu
                420                 425                 430
Met Leu Leu Glu Lys Glu Ser Lys Tyr Ile Glu Gln Glu Phe Asn Lys
                435                 440                 445
Leu Tyr Lys Ala Leu Leu Leu Asp Glu Lys Ile Asn Tyr Asn Ser Leu
450                 455                 460
```

-continued

```
Ala His Asp Ser Leu Gln Glu Ser Val Phe Ser Leu Val Asn Ala Ala
465                 470                 475                 480

Thr Gln Ile Val Ser Ser Ser Phe Lys Ser Leu Trp Phe Glu Asn
                485             490             495

Ile Ile Asn Asn Tyr Gln Lys Ile Asp Glu Ser Asp Gln Leu Gly Asp
            500             505             510

Tyr Thr Asn Trp Ala Asn Lys Lys Ala Lys Tyr Leu Phe Glu Thr Leu
        515             520             525

Leu Lys Ala Ile Ser Ala Ser Lys Leu Asn Asn Asn Pro Gly Trp Tyr
    530             535             540

Val Leu Val Lys Ala Phe Asn Asn Val Lys Tyr Asp Leu Asp Gln Leu
545             550             555             560

Thr Asn Asp Glu Ser Thr Tyr Asn Ser His Leu Lys Arg Ala Gln Glu
                565             570             575

Phe Asp Leu Asp Leu Lys Tyr Tyr Asp Gln Leu Tyr Asp Ala Leu Glu
            580             585             590

His Ser Ile Leu Lys Leu Ser Thr Thr Ala Asn Gln Leu Thr Lys Asn
            595             600             605

Leu His Ile Ser Ser Trp Phe Asn Lys Tyr Thr Asp Asp Ile Lys Asp
        610             615             620

Ala Arg Glu Tyr Val Glu Ile Leu Arg Asn Leu Leu Thr Gly Lys Pro
625             630             635             640

Ile Ser Lys Asp Ser Glu Asp Tyr Lys Glu Phe Met Thr Asn Tyr Gln
                645             650             655

Lys Ala Ile Asp Lys Leu Asn Glu Lys Asn Gln Thr Thr Asn Lys Thr
            660             665             670

Leu Glu
```

SUBUNIT VACCINE OF CONTAGIOUS CAPRINE PLEUROPNEUMONIA AND PREPARATION METHOD AND USE THEREOF

CROSS REFERENCE TO RELATED APPLICATION

This application claims the priority of Chinese Patent Application No. 202110110937.4, entitled Subunit vaccine of contagious caprine pleuropneumonia and preparation method and use thereof filed with the China National Intellectual Property Administration on Jan. 26, 2021, which is incorporated herein by reference in its entirety.

TECHNICAL FIELD

The disclosure belongs to the technology field of preparation of animal infectious disease vaccine, and in particular relates to a subunit vaccine of contagious caprine pleuropneumonia and preparation method and use thereof.

BACKGROUND ART

Contagious caprine pleuropneumonia (CCPP) is an important animal disease endangering the world's goat breeding industry and is a notifiable infectious disease of the World Organization for Animal Health (OIE). The main clinical manifestations of contagious caprine pleuropneumonia are fever, cough and dyspnea. The main necropsy lesions are cellulosic pleuropneumonia, pleural effusion and lung hepatization. Contagious caprine pleuropneumonia is a highly contagious infectious disease and has the characteristics of high incidence rate and high mortality in new epidemic areas, which brings serious threats and huge economic losses to the goat breeding industry. A variety of animals such as Capra aegagrus and Pantholops hodgsonii can be infected. Contagious caprine pleuropneumonia is distributed in more than 40 countries or regions around the world and is currently prevalent in Africa, the Middle East, Asia and other countries or regions, causing huge economic losses. The pathogen of the disease is Mycoplasma capricolum subsp. capripneumoniae (Mccp), which has extremely high nutritional requirements and is difficult to cultivate. Early in 1873, there were documents documenting the outbreak of contagious caprine pleuropneumonia, and it was not until 1976 that Macowan first isolated the pathogen Mccp. At present, contagious caprine pleuropneumonia is widespread in China. However, there are few reports on the isolation of Mycoplasma capricolum subsp. capripneumoniae due to the difficulty of pathogen isolation and cultivation and high technical requirements.

Vaccine immunization is an important means to prevent and control the contagious caprine pleuropneumonia. At present, the main vaccines for the prevention and control of the disease are inactivated whole-bacteria vaccines and inactivated tissue vaccines. The preparation methods of inactivated tissue vaccines generally include infecting healthy goats with infected tissue or bacteria culture, collecting tissues from infected goats' lungs, removing trachea, bronchus and other tissues, grinding, filtering, inactivating the tissue, and other procedures. The preparation methods of inactivated tissue vaccines has problems such as complex process, high requirements for laboratory animals, tendency to pollute other pathogens, unstable quality, and limited scale production capacity. Inactivated whole-bacteria vaccines have many advantages over inactivated tissue vaccines, and have gradually become the main means for preventing and controlling contagious caprine pleuropneumonia. However, the inactivated vaccine in the prior arts has the problems such as difficulty in pathogen cultivation, low growth rate, low yield, complex process, high cost, limited scale production, risk of biosafety, and relatively larger adverse effects, which limits its promotion and application. Subunit vaccine is an important research direction of contagious caprine pleuropneumonia. However, to date, there is no report on effective contagious caprine pleuropneumonia subunit vaccine at home and abroad.

SUMMARY OF THE DISCLOSURE

In view of this, the purpose of the present disclosure is to provide a subunit vaccine of contagious caprine pleuropneumonia and preparation method and use thereof. The present disclosure combines the immune proteins with good immune protection effect widely existing in the Mycoplasma capricolum subsp. capripneumoniae strains into subunit vaccine of contagious caprine pleuropneumonia. The subunit vaccine has the advantages of high safety, good immune effect and stability, minor adverse effects and low cost.

The Mycoplasma capricolum subsp. capripneumoniae immunoproteins A, B, C, D and E involved in the present disclosure are classified and screened through comprehensive analysis of cell localization, protein hydrophilicity, antigenicity, signal peptide, transmembrane region, T cell epitope and B cell epitope, etc. based on the Mccp genomics, comparative genomics, proteomics and immunoproteomics, etc. and verified by in vitro and in vivo tests. The above immunoproteins combination may overcome the problems that a single protein is difficult to induce comprehensive humoral and cellular immunity and the protective effect is limited. The subunit vaccine prepared by screening the immunoproteins combination and by combining with adjuvant formulation may induce comprehensive immune response, and provide good protective effect for goats against Mccp infection.

In order to achieve the above-mentioned purpose of the present disclosure, the present disclosure provides the following technical solutions.

In one aspect, the present disclosure provides a combination of Mycoplasma capricolum subsp. capripneumoniae immunoproteins, including Mycoplasma capricolum subsp. capripneumoniae immunoproteins A, B, C, D and E; the mass ratio of Mycoplasma capricolum subsp. capripneumoniae immunoproteins A, B, C, D and E is (0.5-1.5):(0.5-1.5):(0.5-1.5):(0.5-1.5):(0.5-1.5); the amino acid sequences of Mycoplasma capricolum subsp. capripneumoniae immunoproteins A, B, C, D and E are set forth in SEQ ID No.1-SEQ ID No.5.

In one embodiment, concentrations of the Mycoplasma capricolum subsp. capripneumoniae immunoproteins A, B, C, D and E are independently 20-150 µg/mL.

In another aspect, the present disclosure provides a subunit vaccine of contagious caprine pleuropneumonia, wherein the subunit vaccine of contagious caprine pleuropneumonia includes the combination of Mycoplasma capricolum subsp. capripneumoniae immunoproteins and adjuvant.

In one embodiment, the adjuvant is a double adjuvant, and the double adjuvant includes saponin and ISA 201 VG adjuvant.

In one embodiment, final concentration of the saponin is 1.0-4.0 mg/mL.

In one embodiment, the volume of the ISA 201 VG adjuvant is 50%-55% of volume of the subunit vaccine of contagious caprine pleuropneumonia.

In one embodiment, the subunit vaccine of contagious caprine pleuropneumonia further includes a preservative solution, volume of the preservative solution accounts for 0.8%-1.2% of total volume of the combination of Mycoplasma capricolum subsp. capripneumoniae immunoproteins and the saponins, and mass percent content of the preservative in the preservative solution is 0.8%-1.2%.

In another aspect, the present disclosure provides a method for preparing the subunit vaccine of contagious caprine pleuropneumonia, including the following steps:
1) mixing the combination of Mycoplasma capricolum subsp. capripneumoniae immunoproteins and the saponins to obtain a mixture, allowing the mixture to stand to obtain an antigen saponin mixture, temperature for the standing is 2-8° C., time for the standing is 18-48 h, and shaking the mixture once every 2-4 h during the standing;
2) mixing and emulsifying the antigen saponin mixture and the ISA 201 VG adjuvant to obtain the subunit vaccine of contagious caprine pleuropneumonia.

In one embodiment, the method further includes the following steps before mixing the combination of Mycoplasma capricolum subsp. capripneumoniae immunoproteins with the saponins in the step 1): dissolving proteins in the combination of Mycoplasma capricolum subsp. capripneumoniae immunoproteins in PBS buffer solution and mixing; and mixing the preservative solution with the solution after the standing in the step 1) to obtain the antigen saponin mixture.

In yet another aspect, the present disclosure provides the use of the subunit vaccine of contagious caprine pleuropneumonia in the preparation of drugs for preventing and/or treating contagious caprine pleuropneumonia The subunit vaccine of contagious caprine pleuropneumonia provided by the disclosure combines the immune proteins which have with good immune protection effect and widely exist in the Mycoplasma capricolum subsp. capripneumoniae strains into a safe and effective subunit vaccine. Compared with the prior art, the subunit vaccine of contagious caprine pleuropneumonia has the following advantages:

High safety: the present disclosure can avoid the problems of possible incomplete inactivation of pathogen during the production of inactivated vaccine and possible contamination of other pathogens in the inactivated tissue vaccine. The present disclosure has better safety and minor adverse effects after immunization. The method for preparing the subunit vaccine of contagious caprine pleuropneumonia does not involve pathogen and its nucleic acids, which reduces the risk of spread and contamination of pathogens that may exist in the prior methods for preparing inactivated vaccine, and reduces the risk of biological safety.

High efficiency: the subunit vaccine of contagious caprine pleuropneumonia provided by the present disclosure provides good protective effect and significantly reduces the disease incidence rate and mortality, significantly reducing the lung lesions and bacterial load. The vaccine provided by the present disclosure induces goats to produce good protective effect, and the proteins A, B, C, D and E in the combination of Mycoplasma capricolum subsp. capripneumoniae immunoproteins has good immunogenicity. Furthermore, the adjuvant is selected from saponin and a new type of genetically engineered vaccine adjuvant ISA 201 VG. Saponins are capable of enhancing immune response, stimulating immune reaction of cellular and humoral immune response, and the immune duration is long. ISA 201 VG is a new type of adjuvant, is a water-in-oil-in-water emulsion, which has the advantages of good immune effect, stability, low viscosity, easy injection and small stimulation reaction. Combined use of saponin and ISA 201 VG adjuvant may improve immune response, stimulate cellular and humoral immune response, improve immune protection effect, reduce immune adverse effects, and provide good immune protection effect.

Large-scale production: production of the inactivated whole-bacteria vaccine needs large-scale cultivation of pathogen Mccp which is difficult to cultivate and has a slow growth speed and a low yield. The inactivated whole-bacteria vaccine needs to be concentrated, inactivated, emulsified and subjected other steps to prepare, the process is complicated, and the large-scale production capacity is limited. The preparation methods of inactivated tissue vaccines generally includes infecting healthy goats with infected tissue or bacteria culture, collecting tissues from infected goats' lungs, removing trachea, bronchus and other tissues, grinding, filtering, inactivating, and other procedures. The preparation methods of inactivated tissue vaccines are complicated and difficult to scale-up. The present disclosure directly adopts Mycoplasma capricolum subsp. capripneumoniae immunoproteins which may be highly expressed by prokaryotic system, and the process is relatively simple and prone to large-scale production.

High stability: compared with the inactivated vaccine, the subunit vaccine of contagious caprine pleuropneumonia provided by the present disclosure has less antigen components, higher antigen purity, and it is an water-in-oil-in-water emulsion and has good stability, and it is convenient to transport and preserve.

Minor adverse effects: the inactivated vaccines in the prior arts have many antigen components, because a large amount of animal serum is used in antigen culture, adverse effects are easy to occur after immunization. Because the inactivated tissue vaccine contains animal tissues has complex the compositions, and the adverse effects are relatively large. The subunit vaccine of contagious caprine pleuropneumonia provided by the present disclosure has less antigen components and higher antigen purity, and is made into water-in-oil-in-water emulsion with low viscosity. It is easy to inject and has minor stimulation and adverse effects.

Lower cost: the pathogen of Mccp is difficult to culture, having slow growth rate, low yield and high culture. The bacteria inactivated vaccines in the prior arts need to cultivate a large number of bacteria, and the production cost is high due to the need for concentration, inactivation and other steps. In the present disclosure, *Escherichia coli* is used to efficiently express antigen with high efficiency and low cost.

DETAILED DESCRIPTION OF THE EMBODIMENTS

Figure 1:
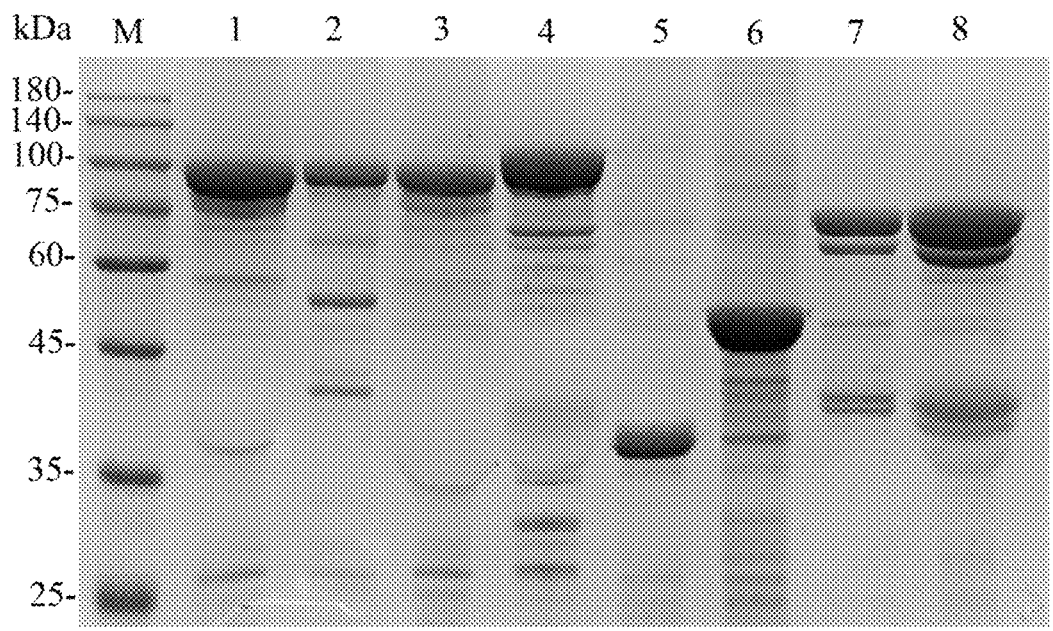
FIG. 1 shows the SDS-PAGE electrophoretic map of recombinant proteins; in the figure, M is the standard for protein molecular weight, lanes 1-3 are for protein C, lane 4 is for protein D, lane 5 is for protein B, lane 6 is for protein A, and lanes 7-8 are protein E.

The present disclosure provides a combination of Mycoplasma capricolum subsp. capripneumoniae immunoproteins, including Mycoplasma capricolum subsp. capripneumoniae immunoproteins A, B, C, D and E; the mass ratio of Mycoplasma capricolum subsp. capripneumoniae immunoproteins A, B, C, D and E is (0.5-1.5):(0.5-1.5):(0.5-1.5):(0.5-1.5):(0.5-1.5); preferably 1:1:1:1:1. In the present disclosure, concentrations of the Mycoplasma capricolum subsp. capripneumoniae immunoproteins A, B, C, D and E are independently 20-150 μg/mL, more preferably 30-100 μg/mL. In the present disclosure, there is no special limitation on the solvents of the Mycoplasma capricolum subsp. capripneumoniae immunoproteins A, B, C, D and E, and any conventional protein solvent in the art can be used. During the specific implementation process of the present disclosure, the solvent is PBS buffer. In the present disclosure, there is no special limitation on the method for preparing the Mycoplasma capricolum subsp. capripneumoniae immunoproteins A, B, C, D and E. They can be prepared by conventional artificial synthesis and recombinant expression by prokaryotic or eukaryotic expression system in the art. During the specific implementation process of the present disclosure, the method for preparing the Mycoplasma capricolum subsp. capripneumoniae immunoproteins A, B, C, D and E is preferably the method of recombinant expression by prokaryotic expression system. In the present disclosure, there is no special limitation on the method of recombinant expression by prokaryotic expression system, and can adopt the conventional method in the art. The detailed steps are as described in the examples.

In the present disclosure, the amino acid sequences of Mycoplasma capricolum subsp. capripneumoniae immunoproteins A, B, C, D and E are set forth in SEQ ID No.1-SEQ ID No.5, and the details are as follows:

```
The amino acid sequence of protein A (SEQ ID No. 1):
MKTKNQEEEIPNGDAFKGAKSLEKKLSPFSDNTIETQQAGLSRVFIKASKKAYSN

NQDDFKNAIERTGGLFILDKNYQDIFFNEELMKIIGVGEVYSKNSSDKRINKKLTLEEFLG

EAKAESLQPANFSNKNSPFVSFNLKNEYLKNLIDPKKNKDNNSLTMITSVGHVIETLRTY

YKKANSTNKQVIEKYLNTYFNQIIKPIQDYISSHLSDALAVKTLKDLFSIEYSTTTTEGTSG

NLAIQRTSLVDSKINKWWKSNQTGKIENTSDLKYVLFGTNNLDKKNDRHIFRFTNSANK

FLYDANASEKDFIKDDKGNVGKYYNKLKISSDNSISQDEELDYIDKVSNKLISIIMTEILFK

KDTTDKDHVVNRNLDQALFRNNVLLHNNQISPDNTRIVTTNPAIVTDRKTQTTKLYIPV

WSNTMAKQVESDILQTSLGYTFKVLSIKEFSSDILE.

The amino acid sequence of protein B (SEQ ID No. 2):
MSNSSSDQITNFYKQKQDQIAEVKLSNKQDLEYYSLRDEYILFNQYQVNTGLCW

DFASIKSLETALMLANNEMYDFSEASISVLNEHWVADGVFFRTFDNLLNRNGIAFESDFR

FGDLYYFPNTGIYYDKLLDLYKSKYITNLANKLEAYSFYRYSILEKLKQIKEHISKHSALF

VGIDHWQVVKNKVNKQETFQITSGSMGAHAVSIIGWDDNYINNDNSKGAFIVLNSDGFY

DNNDGVNYLPYNSSTIYLDLQGYKFIGDKLISSKGINSSIKNKYFNYYNTKLAKKYTETK

PLNQNVFSWDDQVEIQYQLNDQIADFKRIQTSIFLWQTRCFRLE.

The amino acid sequence of protein C (SEQ ID No. 3):
MSTTSIEKLGRKNFVDEESFKNAFIDPNALPVTEFSEVHNNKRSVKYDPEKNVVK

FNGKEISVDQYLQQYYQKYQALPYLNIRYGSFNFYNQYIEAVSPQEFYKFTKWFMKNVS

WGPEIITLKSFSIVKGVEMSGNSITLGAHSNKNKEETTIKFYPDAFFGTLPIYSNLSGRGNA

YESLTYKLNQQVLTQKDLEGFLANVGNYNSLVNLSQQTINKSYFRGITNVSFLKGQKVF

AYKQENWQSKFSKTYSELEKKRLEDRSSYLFVIPANSLQEARKKLEVKLSEYKKESDPFN

FFEKINPKNVVLEEKTISDAEVKQDNTNKIIDKKLVLTFNDKTNYIIHNAFSDVLTEQMTS

NNRRTYVALKNYVNFSSAKQKLEDKVKNFILQIKENIKLKSNGKEKELEELLKEFESYNN

VVSLLEQKNLTSDILKKVDKKIFESETKFNQILNKPNSNKTFNEKEYYKTDIAYSLPELITL

ETLVQHNNSNKLNWRDFYNLNEFVADRSNILKNGSTEFFVYSKFVKEINANENKKYEEL

KSENDLIAASSKVELIDILTKKSIIKPNISQEEINKIILKVDLFDLKKEGQNLLISLRNTTAEK

ASNKEKFGNKWINISINANAKKDVIRATNDLFAVLEYKKVVVPSVLKEESDLRNPITNKL

EKTFDVFVDAYENLIDELLEKVLYAAQWLEGPHIKKVLDENGVMQYKLENGKYLGFTK
```

-continued

DDRIGLWAILKMSDNNFKGISTDFLKFVGAHEYGHHITLNGAQDLGNKGSDPIFISALTP

GATPDISNYYNREVVDLFLKARTHIKLETKRLLDQFGAIKDYGEYAVFNFAKKDKNGNIN

FDTKDNIGIEKDSDIWGVDIEDPNIRKALSNKKRRFLQDFAGLLAAVKERQKENNLTTDD

DKKWLSAFLE.

The amino acid sequence of protein D (SEQ ID No. 4):
MTLNPTVNSSDQQNQVVKYMYKDKKGVLRFQPASLKMLDGILKDGKGNPIKFD

ISNNGKSVEPIVVKGQKDSEGKYYKIDEVLVHNKDGSPIINVPIGVNLRDENSGYNDKKT

IDFINEKIKVVESTIKSLVVDKYSINGWNNENTRISLDSKIDLNYPAIKNIFGSKVPNNVSE

MYKNIYADYVLNRDVDKGSYKFDEHGEISKVKYYNLDSTKVDRYYNSDTPSSLIYANPS

NYKITDDNVELDFKTILWTLYAAGFVTYGNLINAGSSQVLWLSKDKMYMPNVKLQEAY

TDLYFLSSLPKEYEQIFEAKKVLKWISKYTPLFISSSSNKTGVWNMIDNEGKFVDFNLLIN

ENFTNSIKLQLNYSRVKTLDSNVLNGLFGTFKDFNDNSLEFDEYDKWLDFVTVDLRKAK

YNQKQDRVDWEIDYVKSKVDIDKFKEKYKSEVLDKLDSISSMNDNQKQAFKTFYEKAN

ADKTEQIWANEIMRRFSSSYFAMYNSALSIGEIESNKDLAWIFDSTHGYGDFKKAKFKIK

NPDKSKWEISTDDLLNAYKKLAKDLGVETKQLNLVDSLVFDNKTQLYTDQTMTHIYNR

KFDLLSIFSSLATAQPFHTSPTRDVLDYFYKKTERKVNELFSNYTYNFAEVINRDNLQITYS

PSNHDFGNMPSFLSNISEATTGLEYVVDGTTTAKWKKRAIKINDRNGRNGIVNAILDYEK

LVDSEAKNKAEALNLKYRNSKLSQKSNLSDDSNYDNSYFGKFQSINNGWFKDRWYRDF

LDFKLYDDNGNPIKDETIRIKDLEGKKVDSRVNAFWQFYIQSQGVGKRNISGIWRDANK

DAVAMFGYLSSDVANKANYLAFKNQKTGEIKTIKINKQFSSNMFYYKTQNIENEAKYEA

AKTQEEKDKIRHTLAHEKYNYKDINGQHTGVGFVSWVSDYAIMSKYKNALLTPGQQYS

VYFSSDQKGTKDIIKTDLGNFESIAENGKTFSQAPVRMQKNKQVAKVDKDGTKYYENTL

YVYDQFNGVKLE.

The amino acid sequence of protein E (SEQ ID No. 5):
MKSQGNFISYKQENSSSSSGTSSGGSDTGAGRNTDTGSGSNGGFETFNTRRNREK

DPSFNTFKETIKEKLKKGIEEVKKEIDSFLDKEIKEIGDLKTPDDKNKYFEKIERKTYLTEL

KKFFDKKDSNSFVDKPDEFGFNISFPYIIANLEKLYTATVKFDGKDYSDIKVGKSGDSAK

DIKGSDKKLDYSDVITNDVGKIITDTKAQDNFINSKEFDDVVKGYLATWKNEVKKMIYQ

KQDILEFGKDIFFEPTNGNTTTSENTTQVDQYKVYLDTKKYKSWSEYIKEKISKRFTHFD

LEQNQKFKIVDEAKPTPTPTKPTLPDPTNKPLVPTNPPSSQITQAVEALPNLEPYINYQFAS

YDLSSIGSQLSSSQDEEKDKYFFFLNPINTRFKYTVDSVNGNSVVVRITDQAKSGNSRTYI

YENVQVGKDWRFLMLLEKESKYIEQEFNKLYKALLLDEKINYNSLAHDSLQESVFSLVN

AATQIVSSSSFKSLWFENIINNYQKIDESDQLGDYTNWANKKAKYLFETLLKAISASKLN

NNPGWYVLVKAFNNVKYDLDQLTNDESTYNSHLKRAQEFDLDLKYYDQLYDALEHSIL

KLSTTANQLTKNLHISSWFNKYTDDIKDAREYVEILRNLLTGKPISKDSEDYKEFMTNYQ

KAIDKLNEKNQTTNKTLE.

The present disclosure further provides a subunit vaccine of contagious caprine pleuropneumonia, including the Mycoplasma capricolum subsp. capripneumoniae immunoproteins and adjuvant. In the present disclosure, the adjuvant can be selected from one or more of a chemical immune adjuvant, a microbial immune adjuvant, a plant immune adjuvant and a biochemical immune adjuvant. In the present disclosure, the adjuvant is a double adjuvant, preferably saponin and ISA 201 VG double adjuvant. The mass-volume ratio of the saponins to the Mycoplasma capricolum subsp. capripneumoniae immunoproteins antigen solution is preferably 1-4 mg/mL, more preferably 2 mg/mL. In the present disclosure, there is no special limitation on the source of the saponin, and the conventional commercially available products in the art can be used. The volume of the ISA 201 VG adjuvant is 50%-55%, more preferably 50% of volume of the subunit vaccine of contagious caprine pleuropneumonia. In the present disclosure, there is no special limitation on the source of ISA 201 VG, and the conventional commercially available products in the art can be used.

In the present disclosure, the subunit vaccine of contagious caprine pleuropneumonia further includes a preservative solution, volume of the preservative solution accounts for 0.8%-1.2%, more preferably 1.0% of total volume of the combination of Mycoplasma capricolum subsp. capripneumoniae immunoproteins and saponins. The mass percent content of the preservative in the preservative solution is 0.8%-1.2%, more preferably 1.0%. In the specific implementation of the present disclosure, the preservative is preferably thimerosal.

The present disclosure further provides a method for preparing the subunit vaccine of contagious caprine pleuropneumonia, including the following steps: 1) mixing the combination of Mycoplasma capricolum subsp. capripneumoniae immunoproteins and the saponins to obtain a mixture, allowing the mixture to stand to obtain an antigen saponin mixture, temperature of the standing is 2-8° C., time for the standing is 18-48 h, and shaking the mixture once every 2-4 h during the standing; 2) mixing and emulsifying the antigen saponin mixture and the ISA 201 VG adjuvant to obtain the subunit vaccine of contagious caprine pleuropneumonia.

In the present disclosure, the combination of Mycoplasma capricolum subsp. capripneumoniae immunoproteins and the saponins are mixed to obtain a mixture, the mixture is allowed to stand to obtain an antigen saponin mixture. In the present disclosure, before mixing the combination of Mycoplasma capricolum subsp. capripneumoniae immunoproteins and the saponins, the method preferably further includes the following steps: dissolving proteins of the combination of Mycoplasma capricolum subsp. capripneumoniae immunoproteins in PBS buffer solution and mixing to obtain an immunoprotein antigen solution. After obtaining the immunoprotein antigen solution, it is mixed with saponin, and the ratio of the saponin to the immunoprotein antigen solution is preferably 1-4 mg/mL. In the present disclosure, the temperature for mixing and standing the immunoprotein antigen solution and saponin is preferably 4° C., and time for the standing is preferably 24 hours. The mixture is shaken once every 2-4 h during the standing to promote the complete mixing of the saponins and the antigens. In the present disclosure, the solution after the standing is preferably mixed with a preservative solution to obtain an antigen-saponin mixture.

In the present disclosure, the antigen-saponin mixture is mixed with ISA 201 VG adjuvant and emulsified to obtain the subunit vaccine of contagious caprine pleuropneumonia. In the present disclosure, the volume ratio of the ISA 201 VG adjuvant to the antigen saponin mixture is preferably (50-55):(45-50). In the present disclosure, the emulsifying time is preferably 10-30 min. In the present disclosure, the emulsification is preferably carried out by using an emulsifier. The water-in-oil-in-water (w/o/w) emulsion with slight viscous force obtained after the emulsification is the subunit vaccine of contagious caprine pleuropneumonia.

The present disclosure further provides the use of the subunit vaccine of contagious caprine pleuropneumonia in preparation of drugs for preventing and/or treating contagious caprine pleuropneumonia. The drugs of the present disclosure are used for preventing and/or treating the Mycoplasma capricolum subsp. capripneumoniae infection and related diseases caused by the Mycoplasma capricolum subsp. capripneumoniae infection. The drugs provided by the present disclosure may reduce or prevent the lung damage caused by the Mycoplasma capricolum subsp. capripneumoniae, and reduce the settlement and infection of the Mycoplasma capricolum subsp. capripneumoniae in lung, lymph node and kidney. In the present disclosure, there is no special limitation on the dosage and excipients of the drugs, and the dosage and excipients that are acceptable to the subunit vaccine of contagious caprine pleuropneumonia can be adopted.

The technical solutions provided by the present disclosure will be described in detail below in combination with the embodiments, but they should not be understood as limiting the protection scope of the present disclosure.

Mycoplasma capricolum subsp. capripneumoniae M1601 strain, (GenBank accession number: CP017125.1), was obtained from Lanzhou Veterinary Research Institute, Chinese Academy of Agricultural Sciences, reference: Chen S, Hao H, Zhao P, Thiaucourt F, He Y, Gao P, Guo H, Ji W, Wang Z, Lu Z, Chu Y*, Liu Y*. Genome-Wide Analysis of the First Sequenced Mycoplasma capricolum subsp. capripneumoniae Strain M1601. G3 (Bethesda), 2017, 7(9): 2899-2906.

Main reagents: vector pET30a(+) from Novagen company. *Escherichia coli* BL21 (DE3), IPTG, and kanamycin were purchased from TransGen Biotech; Ni-NTA His bind resin was purchased from QIAGEN Company, and protein marker was purchased from Thermo Fisher Scientific.

The main instrument and equipment: low-temperature high-speed centrifuge was purchased from Eppendorf company, low-temperature and high-speed freezing centrifuge was purchased from Beckman company, ultrasonic disrupter was purchased from Ningbo Xinzhi Stock Biotechnology Co., Ltd., electrophoretic apparatus power supply was purchased from Beijing Liuyi company, protein electrophoretic apparatus, gel imager and microplate reader was purchased from Bio-Rad company, the emulsifying machine was purchased from Fluko company, the biological safety cabinet was purchased from Sujing Antai company, and the water-jacket thermostatic constant incubator was purchased from Shanghai Yiheng Company.

Mccp-infected serum and immune serum were prepared and preserved by Lanzhou Veterinary Research Institute, Chinese Academy of Agricultural Sciences. The Mccp 1801 (M1801) of the present disclosure has been disclosed in the document (Wu Yaqin, Liu Baohong, Yuan Ting, etc. Identification and application of specific molecular target for detection of Mycoplasma capricolum subsp. capripneumoniae. Chinese Veterinary Science. 2020, 50 (10)): 1257-1262), and owned and preserved in Lanzhou Veterinary Research Institute, Chinese Academy of Agricultural Sciences.

Experimental Animals: New Zealand white rabbits were purchased from the Experimental Animal Center of Lanzhou Veterinary Research Institute, Chinese Academy of Agricultural Sciences. Healthy goats were purchased from a goat farm in Gansu Province. The Brucella antibody was tested negative, and the Mccp antigen and antibody were all tested negative before the experiment.

Ethics Statement: animal tests complied with guidelines of the ethical and technical specifications of People's Republic of China and approved by the Animal Ethics Committee and of Lanzhou Veterinary Research Institute, Chinese Academy of Agricultural Sciences.

Example 1

Preparation of Protein A

The codon of the gene encoding Mccp protein A (GenBank: CP017125.1, M1601_02645, the 172-1524 nucleotide sequence from the 5'end, hypothetical protein) was optimized and ligated to the pET30a(+) restriction enzyme sites between NdeI and XhoI to express the protein set forth in sequence SEQ ID No.1. The obtained recombinant expression plasmid was transformed into *Escherichia coli* BL21 (DE3) to obtain recombinant bacteria. The recombinant bacteria were inoculated in a LB liquid medium (containing 50 μg/mL kanamycin), cultured at 37° C. and 200 rpm to $OD_{600}$ of 0.6. IPTG having a final concentration of 0.05 mM was added and induced for 12 h at 16° C. and 120 rpm, the recombinant protein culture was centrifuged for 30 minutes at 4° C. and 12000 rpm, bacteria precipitates were collected and resuspended with pre-cooled Lysis buffer (50 mM $Na_2HPO_4$, 0.3 M NaCl, 10 mM imidazole, pH=8.0), and ultrasonically disrupted for 30 minutes (ultrasound 2 s, interval 2 s), centrifuged for 30 min at 4° C. and 7500 rpm. The supernatant was collected and filtered with a 0.45 μm filter for later use. The supernatant was purified with Ni-NTA His bind resin purchased from QIAGEN company, eluted with elution buffer (50 mM $Na_2HPO_4$, 0.3 M NaCl, 250 mM imidazole, pH=8.0) to obtain the target protein. The target protein was dialyzed with a dialysis bag to remove imidazole and saved at −80° C. for later use. The SDS-PAGE results of protein A are shown in FIG. 1.

Preparation of Protein B

The codon of the gene encoding Mccp protein B (GenBank: CP017125.1, M1601_03335, the 85-1089 nucleotide sequence from the 5'end, hypothetical protein), was optimized and ligated to the pET30a(+) restriction enzyme sites between NdeI and XhoI to express the protein set forth in sequence SEQ ID No.2. The obtained recombinant expression plasmid was transformed into *Escherichia coli* BL21 (DE3) to obtain recombinant bacteria. The recombinant bacteria were inoculated in a LB liquid medium (containing 50 μg/mL kanamycin), cultured at 37° C. and 200 rpm to $OD_{600}$ of 0.6. IPTG having a final concentration of 0.05 mM was added. The recombinant bacteria were induced for 6 h at 26° C. and 180 rpm, the recombinant protein culture was centrifuged for at 12000 rpm for 30 minutes at 4° C. and bacteria precipitates were collected and resuspended with pre-cooled Lysis buffer (50 mM $Na_2HPO_4$, 0.3 M NaCl, 10 mM imidazole, pH=8.0), and ultrasonically disrupted for 30 minutes (ultrasound 2 s, interval 2 s), centrifuged for 30 min at 4° C. and 7500 rpm. The precipitates were collected. Inclusion body proteins was purified using an inclusion body wash solution I (Tris 50 mM, NaCl 100 mM, EDTA 2 mM, 0.5% TritionX-100, pH8.0), inclusion body wash solution II (inclusion body wash solution, 1M urea), inclusion body wash solution III (inclusion body wash solution I, 2M urea), inclusion body wash solution IV (inclusion body wash solution I, 3M urea) and inclusion body wash solution V (inclusion body wash solution I, 4M urea) to remove the impure protein. The precipitates were resuspended with resuspension ($Na_2HPO_4$ 50 mM, Tris 1 mM, urea 8M, pH=8.0) and allowed to stand overnight. The inclusion bodies were denatured and dissolved. Dissolving solution was centrifuged for 15 min at 4° C. and 7000 rpm. The supernatant was collected. The purified protein was obtained, dialyzed with dialysis bag to remove urea, filtered with a 0.45 μm filter and saved at −80° C. for later use. The SDS-PAGE results of protein B are shown in FIG. 1.

Preparation of Protein C

The codon of the gene encoding Mccp protein C (GenBank: CP017125.1, M1601_00615, the 106-2823th nucleotide sequence from the 5'end, hypothetical protein) was optimized and ligated to the pET30a(+) restriction enzyme sites between NdeI and XhoI to express the protein set forth in sequence SEQ ID No.3. The obtained recombinant expression plasmid was transformed into *Escherichia coli* BL21 (DE3) to obtain recombinant bacteria. The monoclonal recombinant bacteria was inoculated in a LB liquid medium (containing 50 μg/mL kanamycin), cultured at 37° C. and 200 rpm to $OD_{600}$ of 0.6. IPTG having a final concentration of 0.05 mM was added. The recombinant bacteria were induced for 12 h at 16° C. and 120 rpm, the recombinant protein culture was collected by high-speed centrifugation at 4° C. and 12000 rpm. The bacteria precipitates were resuspended with pre-cooled Lysis buffer (50 mM $Na_2HPO_4$, 0.3 M NaCl, 10 mM imidazole, pH=8.0), and ultrasonically disrupted for 30 minutes (ultrasound 2 s, interval 2 s), centrifuged for 30 min at 4° C. and 7500 rpm after ultrasonic disruption. The supernatant was collected, and filtered by a 0.45 μm filter for later use. The supernatant was purified with Ni-NTA His bind resin purchased from QIAGEN company, eluted with elution buffer (50 mM $Na_2HPO_4$, 0.3 M NaCl, 250 mM imidazole, pH=8.0) to obtain the target protein. The target protein was dialyzed with a dialysis bag to remove imidazole, filtered with a 0.45 μm filter, and saved at −80° C. for later use. The SDS-PAGE results of protein C are shown in FIG. 1.

Preparation of Protein D

The codon of the gene encoding Mccp protein D (GenBank: CP017125.1, M1601_00615, the 2862-5895 nucleotide sequence from the 5'end, hypothetical protein) was optimized and ligated to the pET30a(+) restriction enzyme sites between NdeI and XhoI to express the protein set forth in sequence SEQ ID No.4. The obtained recombinant expression plasmid was transformed into *Escherichia coli* BL21 (DE3) to obtain recombinant bacteria. The monoclonal recombinant bacteria was inoculated in LB liquid medium (containing 50 μg/mL kanamycin), cultured at 37° C. and 200 rpm to $OD_{600}$ of 0.6. IPTG having a final concentration of 0.05 mM was added. The recombinant bacteria were induced for 12 h at 16° C. and 120 rpm, the recombinant protein culture was centrifuged at high speed, 4° C. and 12000 rpm and the bacteria precipitates were collected. The bacteria precipitates were resuspended with pre-cooled Lysis buffer (50 mM $Na_2HPO_4$, 0.3 M NaCl, 10 mM imidazole, pH=8.0), and ultrasonically disrupted for 30 minutes (ultrasound 2 s, interval 2 s), centrifuged for 30 min at 4° C. and 7500 rpm. The supernatant was collected and filtered with a 0.45 μm filter for later use. The supernatant was purified with Ni-NTA His bind resin purchased from QIAGEN company, eluted with elution buffer (50 mM $Na_2HPO_4$, 0.3 M NaCl, 250 mM imidazole, pH=8.0) to obtain the target protein. The target protein was dialyzed with dialysis bag to remove imidazole, filtered by a 0.45 μm filter, and saved at −80° C. for later use. The SDS-PAGE results of protein D are shown in FIG. 1.

Preparation of Protein E

The codon of the gene encoding Mccp protein E (GenBank: CP017125.1, M1601_01955, the 97-2109 nucleotide sequence from the 5'end, hypothetical protein) was optimized and ligated to the pET30a(+) restriction enzyme sites between NdeI and XhoI to express the protein set forth in sequence SEQ ID No.5. The obtained recombinant expression plasmid was transformed into *Escherichia coli* BL21 (DE3) to obtain recombinant bacteria. The monoclonal recombinant bacteria was inoculated in a LB liquid medium (containing 50 μg/mL kanamycin), cultured at 37° C. and 200 rpm to $OD_{600}$ of 0.6. IPTG having a final concentration of 0.05 mM was added and induced for 12 h at 16° C. and 120 rpm, the recombinant protein culture was centrifuged at high speed at 4° C. and 12000 rpm, the bacteria precipitates were collected and resuspended with pre-cooled Lysis buffer (50 mM Na$_2$HPO$_4$, 0.3 M NaCl, 10 mM imidazole, pH=8.0), and ultrasonically disrupted for 30 minutes (ultrasound 2 s, interval 2 s), centrifuged at 4° C. and 7500 rpm for 30 min. The supernatant was collected, and filtered with a 0.45 μm filter for later use. The supernatant was purified with Ni-NTA His bind resin purchased from QIAGEN company, eluted with elution buffer (50 mM Na$_2$HPO$_4$, 0.3 M NaCl, 250 mM imidazole, pH=8.0) to obtain the target protein. The target protein was dialyzed with a dialysis bag to remove imidazole, filtered with a 0.45 μm filter, and saved at −80° C. for later use. The SDS-PAGE results of protein E are shown in FIG. 1.

Example 2

Three healthy New Zealand white rabbits each were immunized with the protein A, protein B, protein C, protein D, and protein E prepared in Example 1, and polyclonal antibodies were prepared. In the first immunization, protein A, protein B, protein C, protein D and protein E were respectively mixed with Freund's complete adjuvant in equal volume and emulsified. Rabbits were subcutaneously immunized at multiple points. Each rabbit was immunized with about 800 μg recombinant protein. The second immunization was carried out 2 weeks later, the third immunization was carried out 3 weeks later, and the fourth immunization was carried out 5 weeks later. The emulsions of protein A, protein B, protein C, protein D and protein E respectively mixed with Freund's incomplete adjuvant were used to enhance immune response. Each rabbit was immunized with 600 μg of recombinant protein. Blood was collected from the ear vein to separate the serum on the 7th day after the last immunization. The prepared polyclonal antibodies of protein A, protein B, protein C, protein D, and protein E were diluted at a dilution ratio of 1:80,000 and western test was carried out with the corresponding recombinant protein, and the results were all positive. The results showed that protein A, protein B, protein C, protein D and protein E can induce the body to produce antibodies at a high level. The polyclonal antibody to the recombinant protein reacts well with Mccp whole bacteria protein in western test. The prepared recombinant protein reacts well with Mccp-infected serum and immune serum in western test, indicating that the recombinant protein has good antigenicity and immunogenicity.

Example 3

The protein A, protein B, protein C, protein D, and protein E prepared in Example 1 were aseptically mixed at 1:1:1:1:1. The final concentration of protein A, protein B, protein C, protein D, and protein E in immunoprotein combination solution (27.88 mL) was 65 μg/mL; 0.54 mL of saponins having a final concentration of 2.0 mg/mL was added. The mixture was allowed to stand at 4° C. for 24 h, shaken once every 4 h during the period. 0.28 mL of 1% thimerosal aqueous solution was added at 1% of total volume of antigen to obtain a mixture of antigen saponins. 28.44 mL of ISA 201 VG adjuvant was taken and 28.44 mL of antigen saponins mixture was added to mix with the ISA 201 VG adjuvant. The mixture obtained was emulsified for 20 minutes with a small emulsifying machine Fluko at gear 1 (5000 rpm). As a result, a sterile slightly viscous water-in-oil-in-water type (w/o/w) vaccine was obtained.

Example 4

Ten (10) healthy goats (Mccp antibody, antigen negative) aged 8-9 months were divided into a vaccine group and a control group, each with 5 goats. Each goat in the vaccine group was injected 2 mL of the vaccine in Example 3 in the neck muscle. Each goat in the control group was injected the same amount of PBS. The goats were observed continuously for 14 days. The results show that after the vaccine of the present disclosure is injected, all the injected goat are healthy, the goat have no symptoms such as coughing, sneezing, no obvious lumps at the injection site, no obvious adverse effects, which indicates that the vaccine is safe.

Example 5

Figure 2:
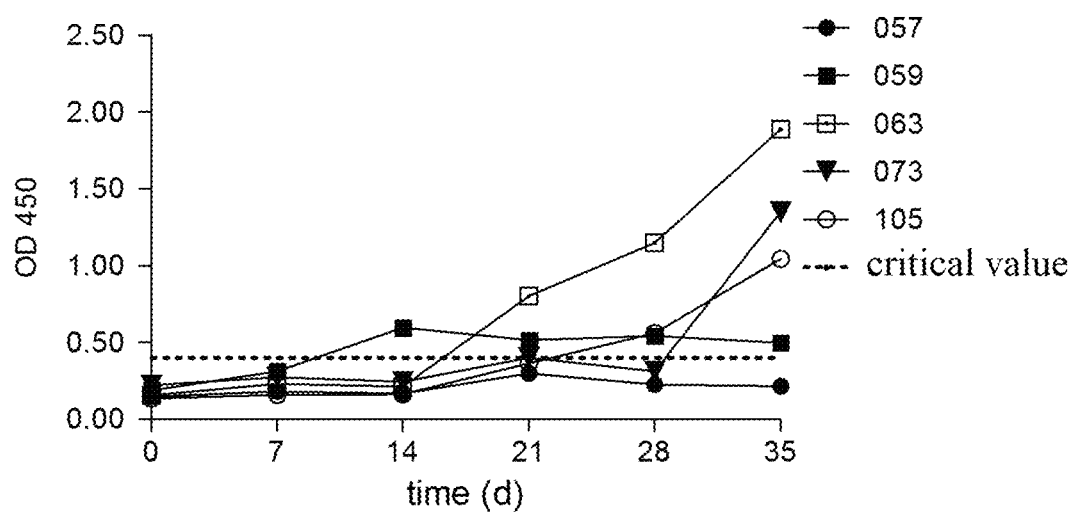
FIG. 2 shows the level of Mccp antibody in goat serum after immunization with the subunit vaccine of the present disclosure.

After immunization in Example 4, the non-anticoagulative blood was collected weekly, and the serum was separated. The Mccp antibody level in serum was determined by indirect ELISA method (coated with Mccp whole bacterial proteins) The operation method is outlined as follows: ultrasonic lysis of Mccp M1801 whole bacteria proteins were diluted to 1.6 μg/mL with 0.05M pH 9.6 carbonate coating solution, 100 μL per well, the ELISA plate was sealed, and incubated at 37° C. for 1 h and then incubated overnight at 4° C. 300 μL PBST wash solution was added to each well to wash 3 times at room temperature and the plate wells was patted dry. 100 μL of solution of 5% dry skim milk powder was added to each well. The plate was sealed for 2 h at 37° C., washed 3 times, patted dry. The primary antibody was incubated. The serum to be tested was diluted with blocking solution at the ratio of 1:200. Negative and positive controls were created and at least two replicates for each sample were made, 100 μL per well. The primary antibody was incubated at 37° C. for 1 h, washed 4 times, patted dry. A HRP-conjugated rabbit anti-goat IgG secondary antibody was diluted with blocking solution at a ratio of 1:5000, 100 μL for each well, incubated for 1 h at 37° C., washed 4 times and patted dry. 100 μL of TMB was added to each well in dark condition and color reaction was perform at 37° C. for 10 min. 100 μL of 2 M H2504 stop solution was added to each well, the solution turned from blue to yellow. The OD value at wave length 450 nm in the microplate reader was read to detect the antibody level in serum. As a result, the Mccp antibodies of the control group are all negative. The subunit vaccine provided by the present disclosure immunized animals can induce higher levels of antibodies (FIG. 2, Table 1, wherein 057, 059, 063, 073, and 105 are animal numbers).

TABLE 1

Mccp antibody level in serum for the goats after the immunization of subunit vaccine provided by the present disclosure

| Immu. day | Animal No. | | | | |
| --- | --- | --- | --- | --- | --- |
| | 057 | 059 | 063 | 073 | 105 |
| | | | OD Value | | |
| day 0 | 0.147 | 0.189 | 0.158 | 0.222 | 0.136 |
| day 7 | 0.182 | 0.313 | 0.232 | 0.274 | 0.159 |
| day 14 | 0.168 | 0.597 | 0.214 | 0.244 | 0.164 |
| day 21 | 0.300 | 0.516 | 0.802 | 0.400 | 0.365 |
| day 28 | 0.226 | 0.544 | 1.149 | 0.312 | 0.562 |
| day 35 | 0.215 | 0.498 | 1.887 | 1.350 | 1.044 |

Example 6

Immune and Protective Effect of Vaccine

Healthy goats (Mccp antibody, antigen negative) aged 8-9 months were divided into an inactivated vaccine group, a subunit vaccine group and a challenge control group, each with 5 goats, and 4 goats in blank control group.

Inactivated vaccine group: inactivated vaccine was injected intramuscularly at the neck on day 0 and day 14 of the experiment, 2 mL for each goat. The method for preparing the inactivated vaccine includes: the Mccp M1801 strain was proliferated and cultured in the modified MTB medium (glucose 2 g/L, sodium pyruvate 2 g/L, PPLO broth 21 g/L, yeast extract 100 mL/L with 25% mass percentages, phenol red 2.5 mL/L with 1% mass percentages, horse serum 200 mL/L, 100000 IU penicillin, pH 7.4-7.6), the PBS buffer (0.01M, pH7.2-7.4) was added, and the mixture obtained was centrifuged 3 times, the concentration of the mixture is adjusted to 300 µg/mL, the final concentration of 2 mg/mL saponin was added, and the mixture obtained was inactivated for 24 h, and mixed with the ISA 201 VG adjuvant at a ratio of 1:1.1 and emulsified to prepare a inactivated whole-bacteria vaccine.

The subunit vaccine group: the vaccine prepared in Example 3 was injected intramuscularly at the neck on day 0 and day 14 of the experiment, 2 mL for each goat.

The challenge control group: PBS was injected intramuscularly at the neck on day 0 and day 14 of the experiment, 2 mL for each goat.

The blank control group was fed normally without any treatment.

Figure 3:
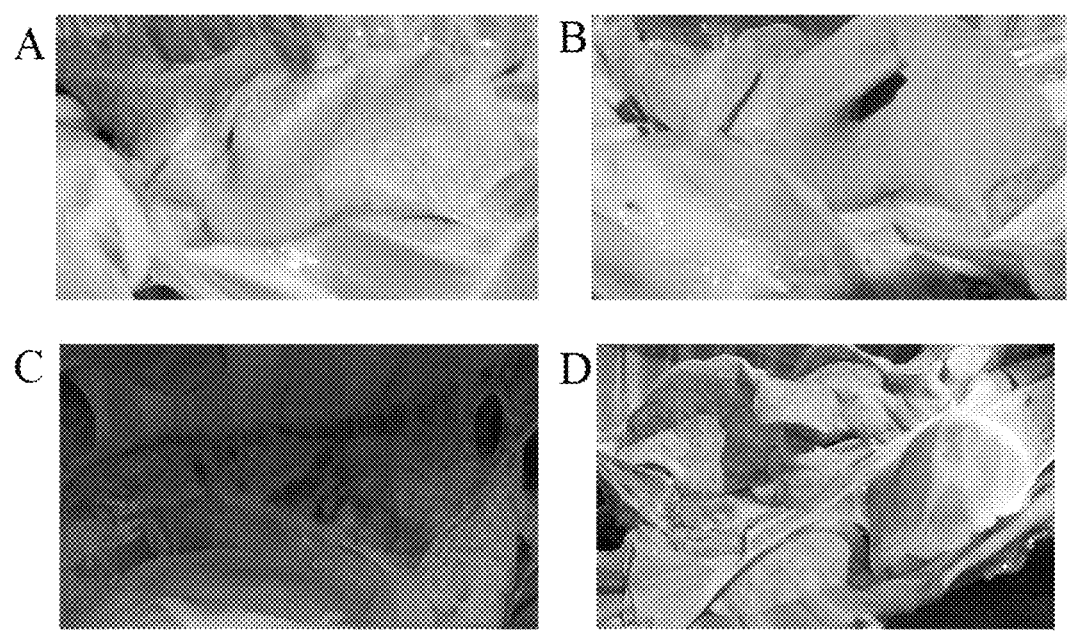
FIG. 3 shows the necropsy lesions of lung dissection; wherein A is the subunit vaccine group of the present disclosure, B is the inactivated vaccine group, C is the challenge control group, and D is the blank control group.

On day 35 of the experiment, the test goats in inactivated vaccine group, the vaccine group and the challenge control group were challenged with Mycoplasma capricolum subsp. capripneumoniae, the culture of strain M1801 (preserved in Lanzhou Veterinary Research Institute, Chinese Academy of Agricultural Sciences, see the document: Wu Yaqin, Liu Baohong, Yuan Ting, etc. Identification and application of specific molecular target for detection of Mycoplasma capricolum subsp. capripneumoniae. Chinese Veterinary Science. 2020, 50 (10)): 1257-1262), and the challenge dose was $10^9$ CCU/mL, the challenge approach was nasal spray of 2 mL for two consecutive days, following injection of 6 mL of bacteria culture through the trachea after 2 days. The results show that some goats have fever and develop symptoms such as cough, sneezing, depression, decreased food intake, etc. The vaccine of the present disclosure can significantly alleviate fever and clinical symptoms after immunization. The blank control group and the immunized animals immunized with subunit vaccine of the present disclosure survive 100%, the inactivated vaccine group survives 80%, and the challenge control group survives 40%. The results show that the vaccine of the present disclosure has good protective effect in the goats infected with Mccp, it can completely resist the attack of vicious Mccp and dramatically reduce the disease incidence and mortality of the goats. The vaccine of the present disclosure can effectively reduce the colonization of Mccp in the lungs of goats. The pathological changes by necropsy of the goats of the challenge control group are mainly pleural effusion, adhesion between lung and chest wall, lungs consolidation, caseous necrosis, gelatum exudates and other typical lesions of CCPP. There are no goats dying in the vaccine group. After the completion of the experimental observation period, there is no obvious pathological changes, only a few goats have slight pathological changes. The vaccine and inactivated vaccine of the present disclosure can significantly reduce lung and other tissue lesions (FIG. 3), and the subunit vaccine of the present disclosure has better effect in improving lung lesions than the inactivated vaccine. Histopathological observation shows that the goats of the challenge control group mainly shows lymphofollicular hyperplasia in the lung tissue, hyperplasia in the alveolar epithelial cells, infiltration in inflammatory cells, fibroblast hyperplasia, fibrin exudation and other diseases. The serious pathological damage of the lung is detected in the challenge control group, and the subunit vaccine group can significantly reduce the pathological damage of the lung. The results show that the immune protection effect of the subunit vaccine of the present disclosure is better than that of the inactivated vaccine.

The above are only the preferred embodiments of the present disclosure. It should be pointed out that for ordinary persons skilled in the art, a number of improvements and modifications can be made without departing from the principle of the present disclosure, and these improvements and modifications should also be regarded as the protection scope of the present disclosure.

What is claimed is:

1. A subunit vaccine of contagious caprine pleuropneumonia, wherein the subunit vaccine of contagious caprine pleuropneumonia comprises a combination of Mycoplasma capricolum subsp. capripneumoniae immunoproteins and adjuvant,
wherein the combination of Mycoplasma capricolum subsp. capripneumoniae immunoproteins comprises Mycoplasma capricolum subsp. capripneumoniae immunoproteins A, B, C, D and E, the mass ratio of Mycoplasma capricolum subsp. capripneumoniae immunoproteins A, B, C, D and E is (0.5-1.5):(0.5-1.5):(0.5-1.5):(0.5-1.5):(0.5-1.5); the of Mycoplasma capricolum subsp. capripneumoniae immunoproteins A consists of the amino acid sequence set forth in SEQ ID No.1, the Mycoplasma capricolum subsp. capripneumoniae immunoproteins B consists of the amino acid sequence set forth in SEQ ID No.2, the Mycoplasma capricolum subsp. capripneumoniae immunoproteins C consists of the amino acid sequence set forth in SEQ ID No.3, the Mycoplasma capricolum subsp. capripneumoniae immunoproteins D consists of the amino acid sequence set forth in SEQ ID No.4, and the Mycoplasma capricolum subsp. capripneumoniae immunoproteins E consists of the amino acid sequence set forth in SEQ ID No.5.

2. The subunit vaccine of contagious caprine pleuropneumonia according to claim 1, wherein the subunit vaccine of contagious caprine pleuropneumonia further comprises a preservative solution, and the volume of the preservative solution accounts for 0.8%-1.2% of total volume of the combination of Mycoplasma capricolum subsp. capripneumoniae immunoproteins and the saponin, and mass percent content of the preservative in the preservative solution is 0.8%-1.2%.

3. The subunit vaccine of contagious caprine pleuropneumonia according to claim 1, wherein concentrations of the Mycoplasma capricolum subsp. capripneumoniae immunoproteins A, B, C, D and E are independently 20-150 μg/mL.

* * * * *